(12) United States Patent
Koda et al.

(10) Patent No.: US 7,980,116 B2
(45) Date of Patent: Jul. 19, 2011

(54) HYDROGEN GAS SENSOR

(75) Inventors: Hiroshi Koda, Sanda (JP); Kiyonori Ono, Sanda (JP)

(73) Assignee: FIS Inc., Itami-shi (JP)

(*) Notice: Subject to any disclaimer, the term of this patent is extended or adjusted under 35 U.S.C. 154(b) by 603 days.

(21) Appl. No.: 12/078,118

(22) Filed: Mar. 27, 2008

(65) Prior Publication Data

US 2009/0031784 A1   Feb. 5, 2009

(30) Foreign Application Priority Data

Mar. 30, 2007 (JP) ................. 2007-091326

(51) Int. Cl.
*G01N 25/22* (2006.01)
(52) U.S. Cl. .......................... 73/23.2; 422/94
(58) Field of Classification Search .............. 73/23.2, 73/23.21, 258.01, 25.03, 25.01; 422/94–96
See application file for complete search history.

(56) References Cited

U.S. PATENT DOCUMENTS

| | | | | |
|---|---|---|---|---|
| 3,092,799 A * | 6/1963 | Baker | | 338/34 |
| 3,564,474 A * | 2/1971 | Firth et al. | | 338/25 |
| 3,959,764 A * | 5/1976 | Allman | | 338/34 |
| 4,134,818 A * | 1/1979 | Pebler et al. | | 204/406 |
| 4,447,397 A * | 5/1984 | Anouchi et al. | | 422/94 |
| 4,457,954 A * | 7/1984 | Dabill et al. | | 427/125 |
| 4,464,339 A * | 8/1984 | Wilkinson-Tough | | 422/94 |
| 5,457,333 A * | 10/1995 | Fukui | | 257/253 |
| 7,007,542 B2 * | 3/2006 | Wang et al. | | 73/23.21 |
| 7,193,187 B2 * | 3/2007 | Chen et al. | | 219/490 |
| 7,235,171 B2 * | 6/2007 | Taniguchi | | 205/787 |
| 7,526,942 B2 * | 5/2009 | Otani et al. | | 73/25.03 |
| 7,537,737 B2 * | 5/2009 | Abe et al. | | 422/104 |
| 7,566,848 B2 * | 7/2009 | Takahashi | | 219/494 |
| 2002/0146352 A1 * | 10/2002 | Wang et al. | | 422/96 |
| 2003/0024813 A1 * | 2/2003 | Taniguchi | | 204/424 |
| 2003/0190261 A1 * | 10/2003 | Abe et al. | | 422/94 |
| 2006/0289400 A1 * | 12/2006 | Takahashi | | 219/121.36 |
| 2007/0041870 A1 * | 2/2007 | Yamanaka et al. | | 422/58 |

FOREIGN PATENT DOCUMENTS

| | | | |
|---|---|---|---|
| EP | 358925 A2 * | 3/1990 | |
| GB | 2125554 A * | 3/1984 | |
| JP | 53-34599 A | 3/1978 | |

(Continued)

OTHER PUBLICATIONS

Notification of Reasons for Refusal dated Jun. 8, 2010 with English abstract.

*Primary Examiner* — John Fitzgerald
(74) *Attorney, Agent, or Firm* — Edwards Angell Palmer & Dodge LLP

(57) ABSTRACT

The hydrogen gas sensor is a catalytic combustion hydrogen gas sensor with a detection element 1, and is characterized by comprising a measuring circuit configured to selectively provide a normal voltage mode for applying a normal voltage to the detection element 1 and a high voltage mode for applying a high voltage higher than said normal voltage to said detection element 1.

Thereby, upon energization of the hydrogen gas sensor, the detection element 1 can be first applied the high voltage to be rapidly heated to raise a temperature of the detection element 1 immediately. And then, the detection element 1 can be applied the normal voltage to be heated to be kept at a predetermined temperature at which the hydrogen gas is detected.

6 Claims, 8 Drawing Sheets

FOREIGN PATENT DOCUMENTS

| | | |
|---|---|---|
| JP | 63-271151 A | 11/1988 |
| JP | 10-90210 | 4/1998 |
| JP | 11-014579 A | 1/1999 |
| JP | 2000221153 A * | 8/2000 |
| JP | 2003-329631 A | 11/2003 |
| JP | 2004-020377 A | 1/2004 |
| JP | 2006-194851 A | 7/2006 |
| JP | 2008-139092 A | 6/2008 |

* cited by examiner

FIG. 14  — Prior Art —

FIG. 15 — Prior Art —
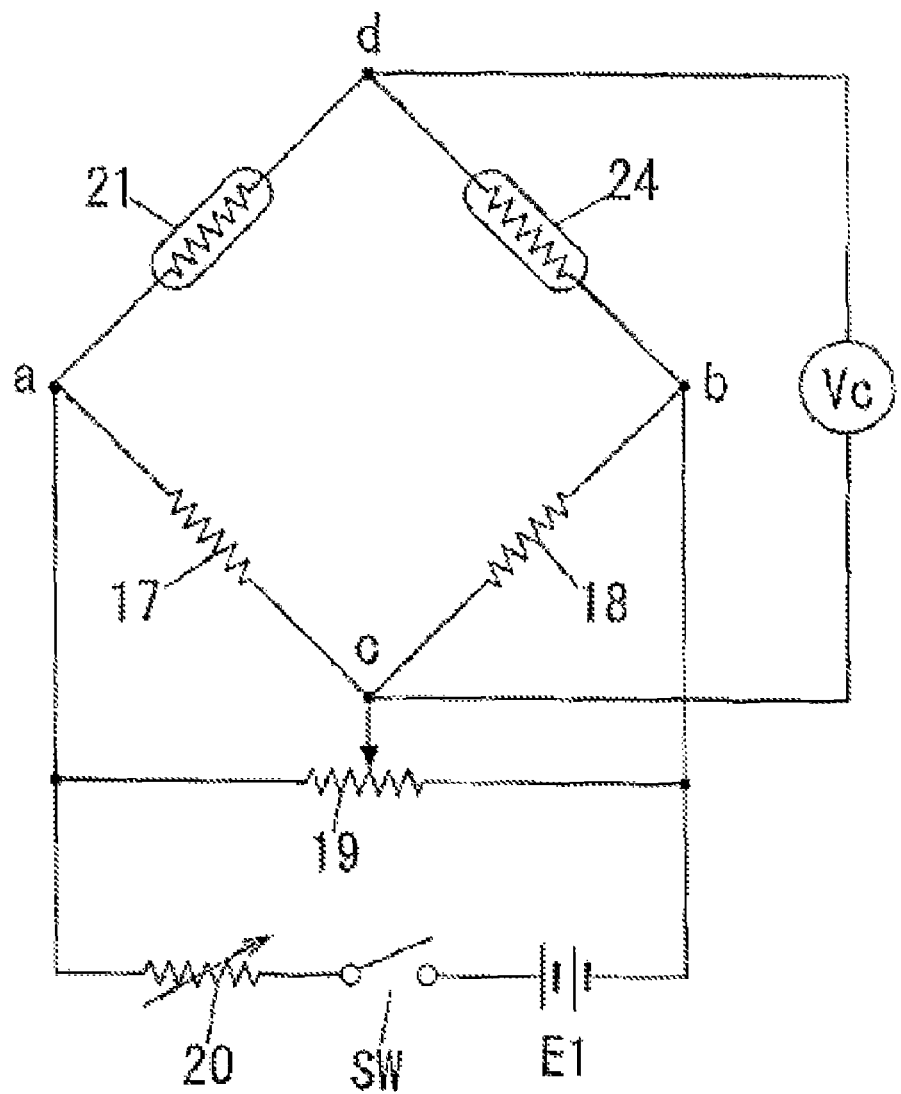

HYDROGEN GAS SENSOR

BACKGROUND OF THE INVENTION

1. Field of the Invention

The present invention relates to a catalytic combustion hydrogen gas sensor which is used for hydrogen gas detection.

2. Description of the Related Art

Hitherto, as a hydrogen gas sensor for detecting a hydrogen concentration in a gas phase, semiconductor gas sensors and catalytic combustion gas sensors are widely used. Particularly, the catalytic combustion gas sensor is a sensor for detecting a hydrogen gas by converting reaction heat produced in burning the hydrogen gas at a sensor surface to electric signals. And the catalytic combustion gas sensor has a feature that its structure is simple and its output signal has a linear characteristic.

A catalytic combustion gas sensor disclosed in Japanese Unexamined Patent Publication No. 10-90210 is shown in FIGS. 14 and 15. A detection element 21 of this gas sensor composes a combustion body 22 for burning a hydrogen gas and a heating resistor 23 for heating the combustion body 22 by the Joule heat produced in accordance with energization of the heating resistor 22.

The combustion body 22 is formed of a directive material such as alumina into bead which contains a combustion catalyst such as palladium or platinum. And, the heating resistor 23 is realized by a metal coil, for example, platinum, having a high temperature coefficient of resistivity.

This detection element 21 is incorporated in a measuring circuit shown in FIG. 15 together with a compensation element 24. The compensation element 24 is formed into almost the same configuration as the detection element 21 except that the combustion body 22 does not contain a catalyst such as palladium or platinum.

The measurement circuit includes a bridge circuit composed of the detection element 21, the compensation element 24, and fixed resistors 17, 18, in order to obtain a voltage Vc across the output terminals "c" and "d", determine resistance variations in the heating resistor 23 from the voltage Vc, and detect the hydrogen gas concentration based on these resistance variations.

A temperature characteristic and a humidity characteristic of the compensation element 24 are almost the same as the detection element 21. But since the compensation element 23 does not have the activity of a combustion catalyst, it does not react with the hydrogen gas. The bridge circuit shown in FIG. 15, comprises a series combination of the detection element 1 and the compensation element 2 across terminals "a" and "b", and a series combination of the fixed resistances 17, 18, across terminals "a" and "b". And, a variable resistance 19 for adjusting equilibrium is connected between the terminals "a" and "b". And an intermediate tap of the variable resistance 19 is connected to a node between the fixed resistances 17, 18. A direct-current power sources E1 is connected in series a switch SW and a variable resistance 20 across the terminals "a" and "b". Therefore, a voltage being applied across the terminals "a" and "b" is regulated by adjustment of the resistance of the variable resistance 20.

In this measuring circuit, a current passing through the heating resistor 23 varies by adjustment of the variable resistance 20 to regulate an amount of heat produced. When using thus configured hydrogen gas sensor, the resistance values of the variable resistance 20 is first adjusted in an atmosphere containing no hydrogen gas to heat the combustion body 22 to a predetermined temperature (for example, 300 to 500° C.), and variable resistance 19 is adjusted to maintain the equilibrium state of the bridge circuit. Thereafter, when the hydrogen gas arrives at the combustion body 22, the hydrogen gas is burnt and the electric resistance of the heating resistor 23 increases. On the other hand, since the compensation element 24 does not have the activity of a hydrogen combustion catalyst, the hydrogen gas is not burnt in the compensation element 24 and electric resistance of the compensation element 24 does not vary. Therefore, a difference of electric resistance is produced between the detection element 21 and the compensation element 24, and a bridge voltage is generated between the output terminals "c" and "d". Since this bridge voltage is proportion to the gas concentration of the hydrogen gas, the gas concentration of the hydrogen gas is detected by this bridge voltage.

In recent years, such a catalytic combustion hydrogen gas sensor is expected to be used for monitoring the leakage of a hydrogen gas of fuel or monitoring and controlling a proper feed rate of hydrogen to a fuel cell, particularly in fuel cell vehicles.

By the way, generally, in fuel cell vehicles, electric power is supplied to the hydrogen gas sensor from a battery while the fuel cell vehicles are driving. But electric power cannot be supplied to the hydrogen gas sensor continually while the fuel cell vehicles are not driving in order to prevent a battery from going dead, and in the meantime, it becomes impossible to detect a hydrogen gas by a hydrogen gas sensor. Accordingly, in order to detect a hydrogen gas by a hydrogen gas sensor immediately after the start of driving of fuel cell vehicles to monitor the leakage of a hydrogen gas or monitor and control a proper feed rate of hydrogen to a fuel cell, it is required that hydrogen gas is detected precisely upon energization of hydrogen gas sensor.

However, only after a delay from a time of application of voltage to the heating resistor 23 to a time at which the combustion body 22 is heated to a predetermined temperature. Accordingly, it usually took a waiting time of more than a dozen seconds to several tens seconds before the precise hydrogen concentration can be measured after energization of the hydrogen gas sensor.

SUMMARY OF THE INVENTION

In view of the above state of the art, it is an object of the present invention to provide a catalytic combustion hydrogen gas sensor which can quickly measure a hydrogen concentration with precision upon energization of the catalytic combustion hydrogen gas sensor.

A hydrogen gas sensor of the present invention is a catalytic combustion hydrogen gas sensor with a detection element 1, and is characterized by comprising a measuring circuit configured to selectively provide a normal voltage mode for applying a normal voltage to the detection element 1 and a high voltage mode for applying a high voltage higher than said normal voltage to said detection element 1.

According to the present invention, upon energization of the hydrogen gas sensor, the detection element 1 can be first applied the high voltage to be rapidly heated to raise a temperature of the detection element 1 immediately. And then, the detection element 1 can be applied the normal voltage to be heated to be kept at a predetermined temperature at which the hydrogen gas is detected. Therefore upon energization of the hydrogen gas sensor, the temperature of the detection element 1 is raised to a predetermined temperature, at which the hydrogen gas is detected, in a short time upon energization of the hydrogen sensor.

Therefore, it is possible to bring quickly a state in which a hydrogen concentration can be measured with precision upon energization of the hydrogen gas sensor, and the hydrogen gas sensor is suitable particularly for the applications of fuel supply control in on-board fuel cells.

It is prefer that the measuring circuit is configured to first apply the high voltage and subsequently apply the normal voltage to the detection element 1. In this case, as described above, the temperature of the detection element 1 can be raised to a predetermined temperature, at which the hydrogen gas can be detected, in a short time upon energization of the hydrogen gas sensor.

It is also prefer that the measuring circuit is configured to first apply the high voltage which is 160% to 190% of the normal voltage to the detection element 1 for a time period of 0.1 sec to 0.3 sec, and subsequently apply said normal voltage to said detection element. In this case, the time necessary to raise temperature of the detection element 1 to a predetermined temperature, at which the hydrogen gas can be detected, can be further reduced upon energization of the hydrogen gas sensor.

It is also prefer that the detection element 1 is shaped into a bead having an outside diameter of 0.3 mm to 0.6 mm. In this case, the time necessary to raise the temperature of the detection element 1 to a predetermined temperature, at which the hydrogen gas can be detected, can be further reduced upon energization of the hydrogen gas sensor.

It is also prefer that the gas sensor comprising a compensation element 2, and the compensation element 2 is dimensioned to be smaller than the detection element 1. In this case, it is possible to inhibit the heating rate of the detection element 1 from exceeding the heating rate of the compensation element 2 upon energization of the hydrogen gas sensor. Therefore, it is prevented that a detected result which looks as if a hydrogen gas exists even though the hydrogen does not actually exist is obtained.

It is also prefer that the detection element 1 comprises a platinum-made coil and a porous body 4 for entrapping silicon compound covering said coil, the coil being configured to serve as a hydrogen combustion member, a heating member, and a temperature-sensing resistor. In this case, a silicon compound, which damages the platinum-made coil 3 to cause deterioration of the catalyst activity of the platinum-made coil 3, is entrapped or eliminated with the porous body 4. Therefore, while an applied voltage to the detection element 1 is reduced, a reduction in measurement sensitivity can be inhibited, and consequently, it is possible that hydrogen is precisely detected over a long duration.

BRIEF DESCRIPTION OF THE DRAWINGS

FIG. 14 is a partially cutaway perspective view of a detection element showing a prior art; and FIG. 15 is a diagram of a measuring circuit showing a prior art.

DETAILED DESCRIPTION OF THE PREFERRED EMBODIMENT

Hereinafter, the preferred embodiment for carrying out the present invention will be described.

A catalytic combustion hydrogen gas sensor includes a detection element 1, a compensation element 2, and a measuring circuit.

As the detection element 1, an appropriate element can be employed as long as it is a detection element of a catalytic combustion type which is sensitive to the hydrogen gas.

Figure 2:
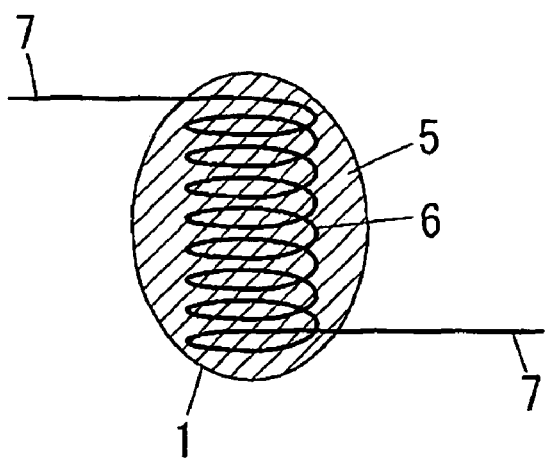
FIG. 2 is a sectional view showing a detection element in the measuring circuit.

An embodiment of the detection element 1 includes, as shown in FIG. 2, the detection element 1 composed of a combustion body 5 for burning a hydrogen gas and a heating resistor 6 for heating the combustion body 5 by the Joule heat produced in accordance with energization of the heating resistor 6. The combustion body 5 is formed of a directive material such as alumina into bead which contains a combustion catalyst such as palladium or platinum. And, the heating resistor 6 is realized by a metal coil, for example, platinum, having a high temperature coefficient of resistivity. The heating resistor 6 is buried in the combustion body 5. Terminal portions 7 composed of the metal wire are extended out from both ends of the heating resistor 6.

In preparing such a detection element 1, fine powder of alumina, silica or the like, and alumina sol or silica sol as a binder are mixed to form a paste, which is applied to a circumference of the heating resistor 6, and is heated and baked to form an inorganic porous body, and an aqueous solution of chloroplatinic acid is applied to the inorganic porous body, and the inorganic porous body is dried with air, and the resulting one is baked at about 800° C., and thereby a combustion body 5 is formed.

In this detection element 1, the combustion body 5 is configured to serve as a hydrogen combustion member which is heated to burn a hydrogen gas. And, the heating resistor 6 is configured to serve as a heating member which is heated by the Joule heat produced in accordance upon being energized. The heating resistor 6 is also configured to serve as a temperature-sensing resistor of which electric resistance varies in response to temperature rise due to combustion heat produced by burning the hydrogen gas in the hydrogen combustion member. The variation in electric resistance is detected as a hydrogen gas concentration and is extracted as a hydrogen concentration signal.

The compensation element 2 gives a resistance which is used to compensate for environmental conditions such as ambient temperature variations, thereby enabling to accurately defect the resistance variation in the detection element 1. The compensation element 2 has the same temperature-resistance characteristic as in the detection element 1 except for not having the activity of a hydrogen combustion catalyst. The compensation element 2 used in combinations with the detection element 1 may include a bead shaped dielectric member of alumina encapsulating the heating resistor 6 but containing no combustion catalyst.

Figure 3:
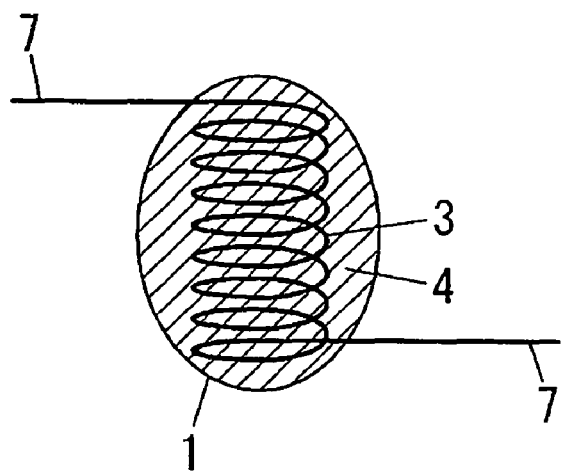
FIG. 3 is a sectional view showing another a detection element which may be used in above.

Further, the detection element 1 may comprise, as shown in FIG. 3, a porous body 4 for entrapping silicon compound, and the platinum-made coil that is embedded into the porous body 4 to serve as a hydrogen combustion member, a heating member, and a temperature-sensing resistor.

The platinum-made coil 3 is realized by a platinum metal coil having catalyst activity, for example, platinum or a platinum alloy like zirconia-stabilized platinum. The terminal portions 7 composed of the metal wire are extended out from both ends of the platinum-made coil 3. It is preferable that an aqueous solution of chloroplatinic acid or an aqueous solution of palladium nitrate is applied onto the surface of the platinum-made coil 3, and thereafter, the platinum-made coil is baked at about 800° C. In this case, the activity of a hydrogen combustion catalyst of the platinum-made coil 3 is improved.

A porous body 4 for entrapping silicon compound is formed so as to cover the platinum-made coil 3. The porous body 4 has the function of entrapping a harmful silicon compound contained within a gas surrounding the porous body 4, thereby keeping the coil free from the silicon compound which would damage the coil 3.

The porous body 4 for entrapping silicon compound may be comprised of a porous body containing a material (hereinafter, referred to as a silicon-entrapping material) having the function of entrapping a silicon compound. Preferably the porous body is made of an inorganic material such as silica or alumina, in which the silicon-entrapping material is dispersed. A platinum content of the porous body 4 for entrapping silicon compound in this case may be in a rage of 5 to 30% by weight.

The compensation element 2 has the same constitution as in the detection element 1 except for not having the activity of a hydrogen combustion catalyst. The compensation element 2 comprises a porous body 4 for entrapping silicon compound, and a coil that is embedded into the porous body 4. The coil is the same as the platinum-made coil 3 but without the catalytic activity. For the coil is obtained, it is prefer that the platinum-made coil 3 is made damaged in advance with silicone vapor, or a proper amount of a chloroauric acid solution is applied to the surface of the platinum-made coil 3 to alloy platinum at the surface of the platinum-made coil 3 with gold. In this case, the activity of a hydrogen combustion catalyst is eliminated from the platinum-made coil 3.

The detection element 1 of above embodiments is suitably sized. The detection element 1 of less dimensions can be heated to a predetermined temperature sufficient for detection of hydrogen gas in a shorter time upon energization of the hydrogen gas sensor. However, fabrication of a too small element causes difficulties in production and tends to produce variations in the dimension of the element in its mass production. Therefore, the detection element 1 is adapted so as to be preferably 0.3 to 0.6 mm and more preferably 0.4 to 0.5 mm in the dimension of the outside diameter. And, since the compensation element 2 preferably has a similar temperature-resistance characteristic to the detection element 1, it preferably has similar dimensions to the detection element 1. But in order to prevent the malfunction of the hydrogen gas sensor upon energization of the hydrogen gas sensor, the dimension of the compensation element 2 is preferably adapted so as to be smaller than that of the detection element 1 and the outside diameter of the compensation element 2 is more preferably adapted so as to be 90 to 95% of the outside diameter of the detection element 1.

Figure 1:
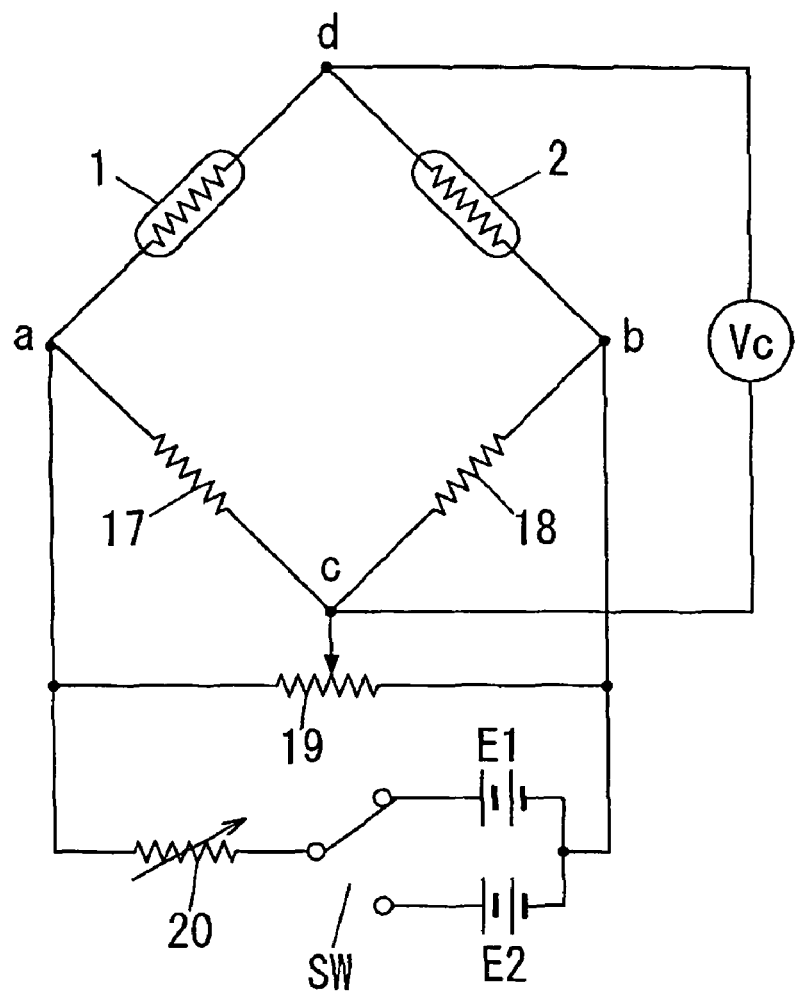
FIG. 1 is a diagram of a measuring circuit utilized in hydrogen gas sensor in accordance with a preferred embodiment of the present invention.

The detection element 1 and the compensation element 2 are incorporated in a measuring circuit shown in FIG. 1.

The measurement circuit includes abridge circuit composed of the detection element 1, the compensation element 2, and fixed resistors 17, 18, in order to obtain a voltage Vc across the output terminals "c" and "d", determine resistance variations in heating resistor 6 or the platinum-made coil 3 from the voltage Vc, and detect the hydrogen gas concentration based on these resistance variations.

A temperature characteristic and a humidity characteristic of the compensation element 2 are almost the same as the detection element 1. But since the compensation element 2 does not have the activity of a combustion catalyst, it does not react with the hydrogen gas. The bridge circuit shown in FIG. 1, comprises a series combination of the detection element 1 and the compensation element 2 across terminals "a" and "b", and a series combination of the fixed resistances 17, 18, across terminals "a" and "b". And, a variable resistance 19 for adjusting equilibrium is connected between the terminals "a" and "b". And an intermediate tap of the variable resistance 19 is connected to a node between the fixed resistances 17, 18. A parallel combination of direct-current power sources E1 and E2 is connected in series a switch SW and a variable resistance 20 across the terminals "a" and "b". Therefore, a voltage being applied across the terminals "a" and "b" is regulated by adjustment of the resistance of the variable resistance 20.

When using thus configured hydrogen gas sensor, the switch SW is turned on to apply the voltage to the detection element 1 and the compensation element 2 with the variable resistance 19 being adjusted to maintain the equilibrium of the bridge circuit. When the hydrogen gas arrives at the detection element 1, the hydrogen gas is burnt and the electric resistance of the heating resistor 6 or the platinum-made coil 3, which is configured to serve as a temperature-sensing resistor, increases. On the other hand, since the compensation element 2 does not have the activity of a hydrogen combustion catalyst, the hydrogen gas is not burnt in the compensation element 2 and electric resistance of the compensation element 2 does not vary. Therefore, an electric resistance difference is produced between the detection element 1 and the compensation element 2 and a bridge voltage is generated between the output terminals "c" and "d". Since this bridge voltage is proportional to the gas concentration of the hydrogen gas, the gas concentration of the hydrogen gas is detected by this bridge voltage.

The measuring circuit is configured to selectively provide a normal voltage mode for applying a normal voltage to said detection element and a high voltage mode for applying a high voltage higher than said normal voltage to said detection element. The switch SW is provided to selectively connect the direct-current power sources E2 and E1 to apply a voltage to the detection element 1 and the compensation element 2. And, the normal voltage in the normal voltage mode is applied to the detection element 1 by one direct-current power source (normal voltage power source) E1 and the high voltage in the high voltage mode is applied to the detection element 1 by the other direct-current power source (high voltage power source) E2.

The normal voltage is a voltage which is continuously applied to the detection element 1 to enable a temperature of the detection element 1 to be kept at a predetermined temperature at which the hydrogen gas is detected. And, the high voltage is higher than the normal voltage preferably by 60 to 90%.

Upon energization of the hydrogen gas sensor, the switch SW is turned on first to provide the high voltage mode at which a voltage is applied to the detection element 1 and the compensation element 2 by the high voltage power source E2. When preferably 0.1 to 0.3 second elapses after the switch SW is turned on, by manipulation of switch SW, the normal voltage power source E1 is selected as a power source to apply a voltage to the detection element 1 and the compensation element 2. Thereby, the normal voltage mode is provided.

Therefore, upon energization of the hydrogen gas sensor, the high voltage is applied to the detection element 1 first, so as to rapidly heat the detection element 1. Subsequently, the normal voltage is applied to the detection element 1 to keep the temperature of the detection element 1 at a predetermined temperature for detection of the hydrogen gas. Therefore, the temperature of the detection element 1 is raised to a predetermined temperature, at which the hydrogen gas is detected, in a short time after energization of the hydrogen gas sensor, and it becomes possible to measure a hydrogen gas concentration with precision immediately upon energization of the hydrogen gas sensor.

EXAMPLES

Hereinafter, the present invention will be described in more detail based on examples.

1. Preparation of Element

The detection element 1 and the compensation element 2 for use in a test were prepared as mentioned below.

(1) Preparation of Elements of Specimen (1)

A platinum wire of 20 μm in diameter was wound into the coiled heating resistor 6 having a coil diameter of 150 μm and number of turns of 10.

Fine powder of alumina and alumina sol as a binder were mixed to form a paste, which was applied to a circumference of this heating resistor 6, and was heated and baked at 800° C. to form an inorganic porous body. This inorganic porous body was immersed in liquid droplets of an aqueous solution of chloroplatinic acid (concentration of platinum equivalent basis 30 g/L) and then taken out 3 seconds later. The inorganic porous body was dried with air and baked at 800° C. to form a combustion body 5.

Thereby, a plurality of detection elements 1 having a structure shown in FIG. 2, the outside diameter of which vary in a range of 0.3 to 0.6 mm, were prepared.

A compensation element 2 used in combinations with this detection element 1 was prepared in the same way as in the above-mentioned detection element 1 except for not performing application and baking of an aqueous solution of chloroplatinic acid.

(2) Preparation of Elements of Specimen (2)

A platinum metal wire of 20 μm in diameter was wound into the coiled platinum-made coil 3 having a coil diameter of 150 μm and number of turns of 10. An aqueous solution of chloroplatinic acid having a concentration of 30 g/L was applied onto the surface of the platinum-made coil 3. The platinum-made coil 3 was baked at about 800° C. Thereby the catalyst activity of the surface of the platinum-made coil 3 was improved.

Silica gel powder of 1.0 g, and aqueous solution of chloroplatinic acid having a platinum equivalent weight of 0.2 g were mixed to form a mixture. Water content was evaporated from the mixture. The mixture was baked at 600° C. for 10 minutes in an electric furnace to form a baked body. The baked body was ground with a mortar to form ground powder. 0.3 cm$^3$ of silica sol and a proper amount of water was added to the ground powder to form a pasty mixture.

The pasty mixture was applied to a circumference of the above-mentioned platinum-made coil 3 to cover the whole platinum-made coil 3. This was dried with air and baked at 600° C. for 5 minutes to form a porous body 4 for entrapping silicon compound.

Thereby, a plurality of detection elements 1 having a structure shown in FIG. 3, the outside diameter of which vary in a range of 0.3 to 0.6 mm, were prepared.

A compensation element 2 was prepared in the same way as in the above-mentioned detection element 1 but without being treated by an aqueous solution of chloroplatinic acid to the platinum-made coil 3 and damaged by silicone vapor.

2. Characteristic Evaluation Test with Constant Applied Voltage

On each of specimen (1) and (2), first, the hydrogen sensor was energized in cases where the applied voltages to the detection element 1 were constant.

(1) Specimen (1)

Figure 4:
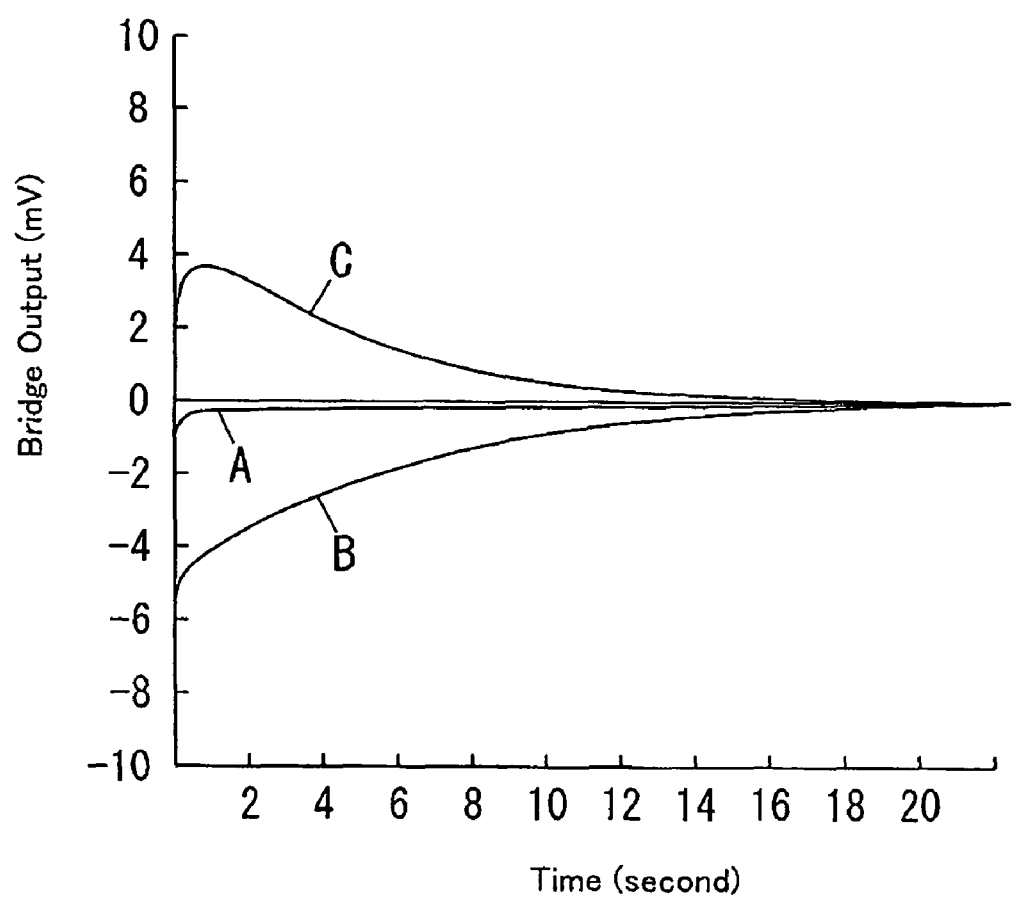
FIG. 4 is a graph showing the results of characteristic evaluation test with constant applied voltage, measured with respect to specimen (1) in the ambient atmosphere.

From the elements of specimen (1), the following combinations of the detection element 1 and the compensation element 2 having an outside diameter of around 0.6 mm, respectively, were selected: that is, a combination (A) of the detection element 1 and the compensation element 2 having the same dimension, a combination (B) of the detection element 1 having larger dimensions than the compensation element 2 and the compensation element 2, and a combination (C) of the detection element 1 having smaller dimensions than the compensation element 2 and the compensation element 2. The detection element 1 and the compensation element 2 of these combinations were incorporated in a measuring circuit shown in FIG. 15. And then, after a voltage of 0.8 V was applied to the detection element 1 in the ambient atmosphere and a bridge output was adjusted to 0V, energization of the measuring circuit was stopped once. Thereafter, energization was re-started and secular changes in the bridge output were measured. The results of measurement are shown in FIG. 4.

Figure 5:
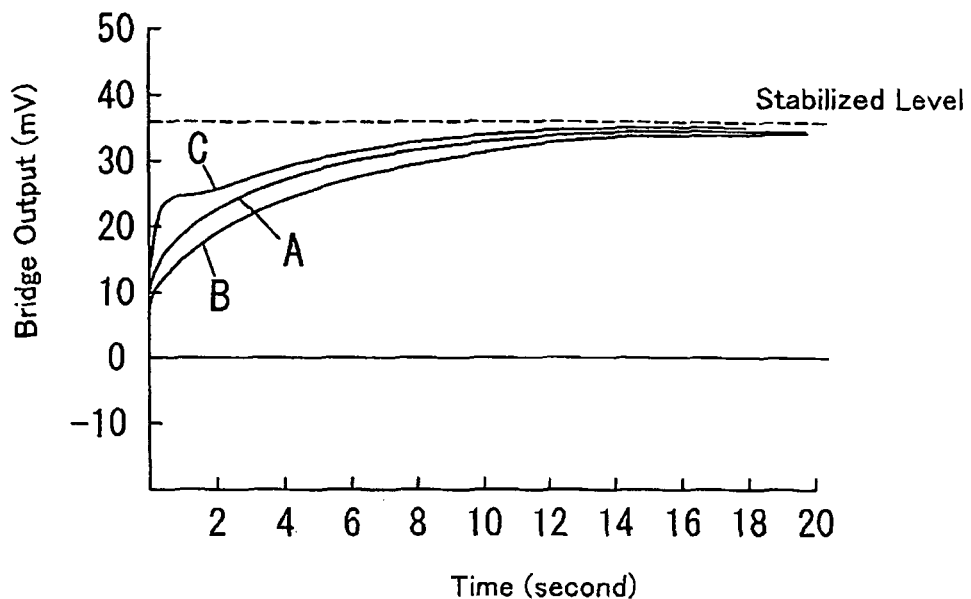
FIG. 5 is a graph showing the results of the characteristic evaluation test with constant applied voltage, measured with respect to specimen (1) in an atmosphere of the hydrogen concentration of 10000 ppm.

And, a similar test was carried out in an atmosphere of a hydrogen concentration of 10000 ppm in place of the test in the ambient atmosphere. The results of the test are shown in FIG. 5.

Consequently, in a case (A) where heat capacity was balanced between compensation element 2 and the compensation element 2 in the ambient atmosphere, the detection element 1 and the compensation element 2 were equal in a temperature raising rate, and consequently the bridge output became a constant value almost instantaneously.

On the other hand, in the case (B) where the detection element 1 is larger than the compensation element 2, since the temperature raising of the compensation element 2 is faster than that of the detection element 1, the bridge output value approaches 0 V from a negative side.

Further, in the case (C) where the detection element 1 is smaller than the compensation element 2, since the temperature raising of the detection element 1 was faster than that of the compensation element 2, the bridge output value approaches 0 V from a positive side.

In the case (B) and (C), upon energization of the hydrogen gas sensor, stabilization time (i.e. time elapsing from re-start of energization to stabilization of the bridge output) was about 20 seconds. This means that it took about 20 seconds for the detection element 1 and the compensation element 2 to reach a constant temperature.

Further, in the atmosphere of the hydrogen concentration of 10000 ppm, the stabilization time was about 15 to 20 seconds in any of the cases (A) to (C). The bridge output values were stabilized near 35 mV in any cases. As for this, it is considered that as much as 15 to 20 seconds are necessary to attain thermodynamic equilibrium between the combustion body 5 heated by combustion of hydrogen, and the heating resistor 6 heated by the Joule heat.

Figure 6:
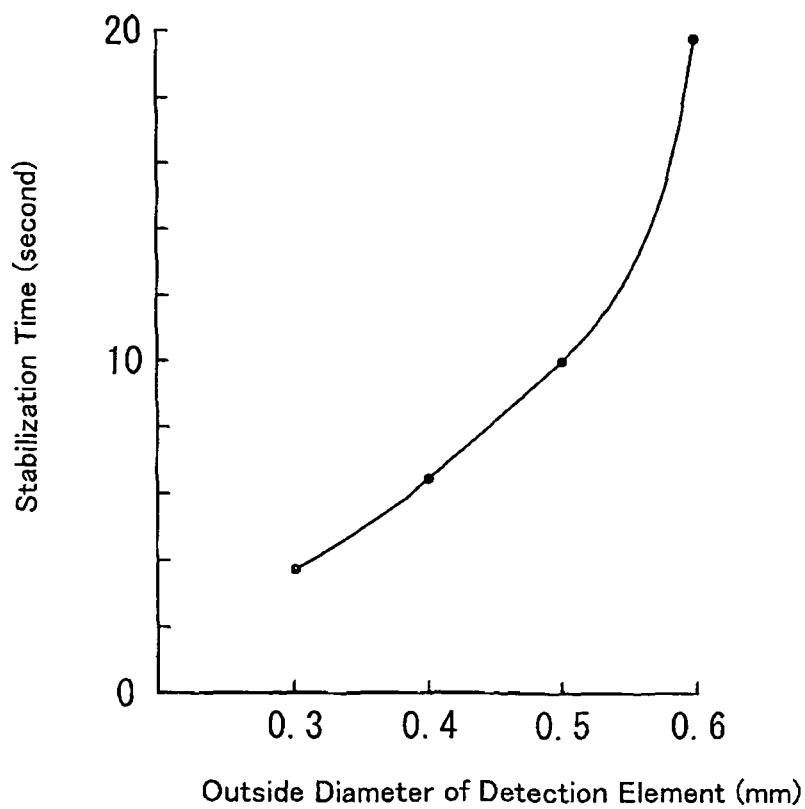
FIG. 6 is a graph showing a relationship between the dimension of an outside diameter of the detection element and stabilization time in the characteristic evaluation test with constant applied voltage, measured with respect to specimen (1) in an atmosphere of the hydrogen concentration of 10000 ppm.

Further, the stabilization time was determined in an atmosphere of a hydrogen concentration of 10000 ppm was determined in the same way as described above also in cases where the outside diameters of the detection elements 1 are 0.5 mm, 0.4 mm and 0.3 mm respectively. The results are shown in FIG. 6 together with the results in the case where the outside diameter is 0.6 mm.

Consequently, the smaller the dimension of the element, the shorter the stabilization time became, but the stabilization time is as much as about 4 seconds even though the outside diameter was 0.3 mm.

Therefore, the stabilization time was not adequately reduced, and these hydrogen sensors could not achieve quick response required particularly for the control of on-board fuel cells.

(2) Specimen (2)

Figure 7:
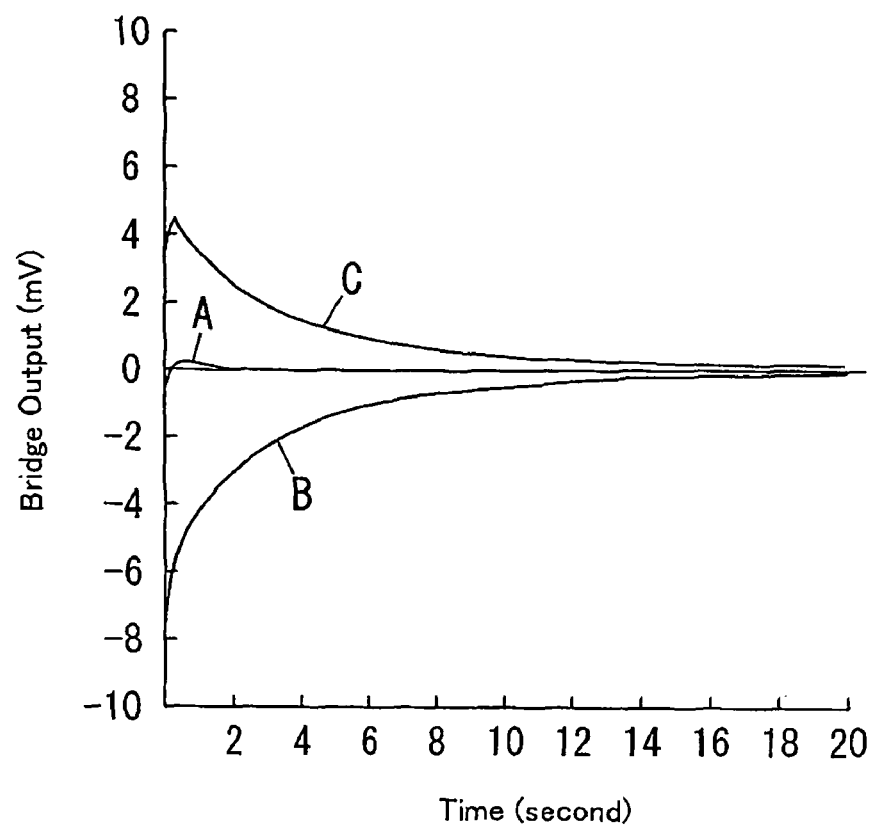
FIG. 7 is a graph showing the results of the characteristic evaluation test with constant applied voltage, measured with specimen (2) in the ambient atmosphere.
Figure 8:
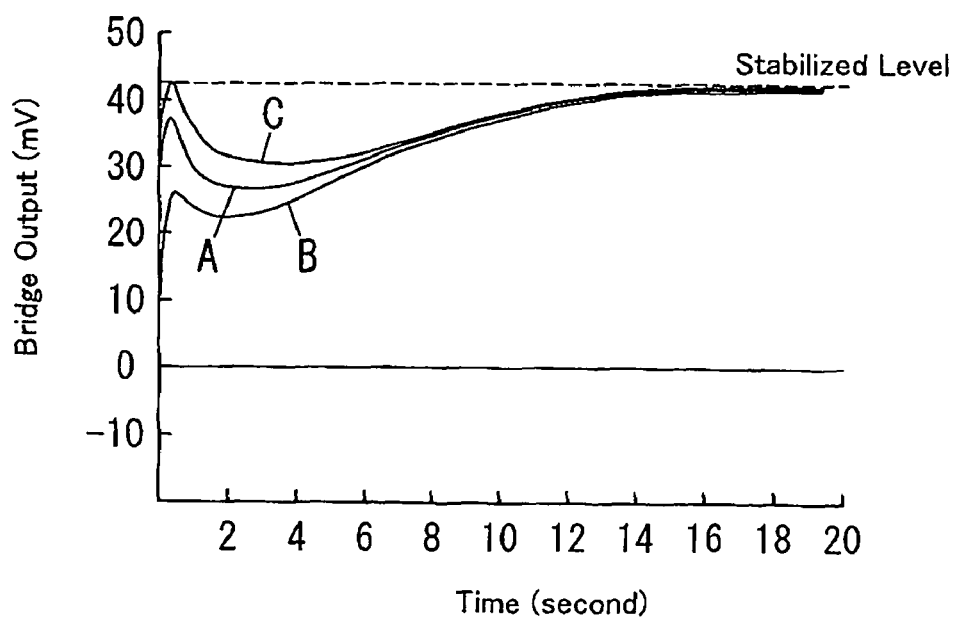
FIG. 8 is a graph showing the results of the characteristic evaluation test with constant applied voltage, measured with specimen (2) in an atmosphere of the hydrogen concentration of 10000 ppm.

The detection element 1 of specimen (2) can function at a lower temperature than that of specimen (1). Therefore, a voltage applied to the detection element 1 of specimen (2) was reduced to 0.5V. An evaluation test of a start up characteristic was carried out by following the same procedure as in the above specimen (1) except for changing the applied voltage. The results of the evaluations in the ambient atmosphere and the results in the atmosphere of the hydrogen concentration of 10000 ppm are shown in FIG. 7 and FIG. 8, respectively.

Figure 9:
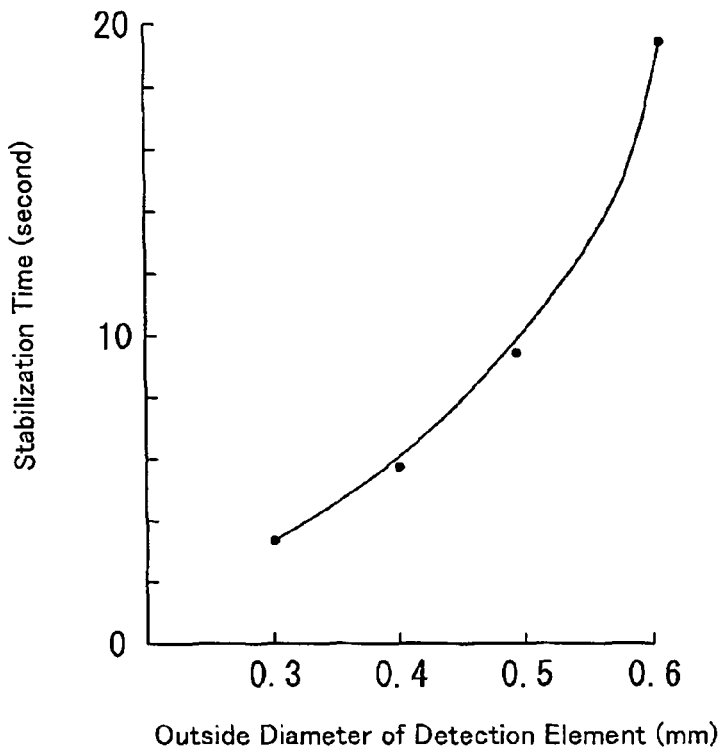
FIG. 9 is a graph showing a relationship between the dimension of an outside diameter of the detection element and the stabilization time in the characteristic evaluation test, measured with specimen (2) in an atmosphere of the hydrogen concentration of 10000 ppm

Further, the stabilization time in an atmosphere of a hydrogen concentration of 10000 ppm was determined in the same way as described above also for cases where the outside diameters of the detection elements 1 were 0.5 mm, 0.4 mm and 0.3 mm. The results are shown in FIG. 9 together with the results in the case where the outside diameter was 0.6 mm.

Consequently, the smaller the dimension of the element, the shorter stabilization time became, but stabilization time is as much as about 4 seconds though the outside diameter was 0.3 mm.

Therefore, the stabilization time was not adequately reduced, and these hydrogen sensors could not achieve quick response required particularly for the control of on-board fuel cells.

In the ambient atmosphere, specimen (2) suffers from similar start up characteristic to specimen (1) as shown in FIG. 7. But, in the atmosphere of the hydrogen concentration of 10000 ppm, specimen (2) suffers from an overshoot in the bridge output immediately after energization as shown in FIG. 8. As for this, it is considered that in the detection element 1 of specimen (2), first, a temperature of the platinum-made coil 3 was raised upon energization by heat produced in accordance with hydrogen combustion, and subsequently this heat was transferred to the porous body 4 to reduce the temperature of the platinum-made coil 3.

3. Characteristic Evaluation Test with Switching of Applied Voltage

The hydrogen sensor was energized in cases where the detection element 1 and the compensation element 2 were incorporated in a measuring circuit shown in FIG. 1 and the high voltage was applied to the detection element 1 first, and then the normal voltage was applied to the detection element 1.

Since in a preliminary experiment, the direction element 1 having the outside diameter of more than 0.6 mm does not stand a chance of adequately improving response in any condition of applying a voltage, this element was excluded from present experimental objects. And, the applied voltage and the application time were studied within proper conditions excluding the conditions under which there is no probability that adequate response is achieved.

(1) Specimen (1)

The circuit where the elements of Specimen (1) were incorporated was adapted in such a way that the high voltage was applied to the detection element 1 in the ambient atmosphere first, and then the normal voltage (0.8 V) was applied to the detection element 1 for each of cases where the outside diameters of the detection elements 1 were 0.4 mm, 0.5 mm and 0.6 mm. The same test as the above characteristic evaluation test with application of constant voltage was carried out except for the above applied voltage pattern.

The high voltage was set at voltage values which were higher than the normal voltage (0.8 V) by 30%, 60%, 90% and 120%. And, the evaluation test was carried out on each of cases where an application time in this high voltage mode was set at 0.1 second, 0.2 second and 0.3 second.

The stabilization time was measured in the same way as in the above characteristic evaluation test with application of constant voltage on the respective cases, and the results of measurement are shown in Table 1.

TABLE 1

| | Conditions of the high voltage mode | | | | |
|---|---|---|---|---|---|
| Outside diameter of the | | Applied voltage (percentage increase in voltage with respect to the normal voltage) | | | |
| detection element | Application time | Increase by 30% | Increase by 60% | Increase by 90% | Increase by 120% |
| 0.4 mm | 0.1 sec | 0.4 sec | 0.4 sec | 0.5 sec | 0.3 sec |
| | 0.2 sec | 0.4 sec | 0.2 sec | 0.3 sec | 0.8 sec |
| | 0.3 sec | 0.4 sec | 0.4 sec | 0.6 sec | 0.7 sec |
| 0.5 mm | 0.1 sec | 0.6 sec | 0.7 sec | 0.6 sec | 0.7 sec |
| | 0.2 sec | 0.7 sec | 0.5 sec | 0.4 sec | 0.8 sec |
| | 0.3 sec | 0.6 sec | 0.5 sec | 0.5 sec | 0.8 sec |

TABLE 1-continued

| Outside diameter of the detection element | Conditions of the high voltage mode | | | | |
|---|---|---|---|---|---|
| | | Applied voltage (percentage increase in voltage with respect to the normal voltage) | | | |
| | Application time | Increase by 30% | Increase by 60% | Increase by 90% | Increase by 120% |
| 0.6 mm | 0.1 sec | 2.1 sec | 1.0 sec | 0.8 sec | 0.7 sec |
| | 0.2 sec | 1.1 sec | 0.9 sec | 0.8 sec | 0.7 sec |
| | 0.3 sec | 1.0 sec | 0.9 sec | 0.8 sec | 0.9 sec |

Figure 10:
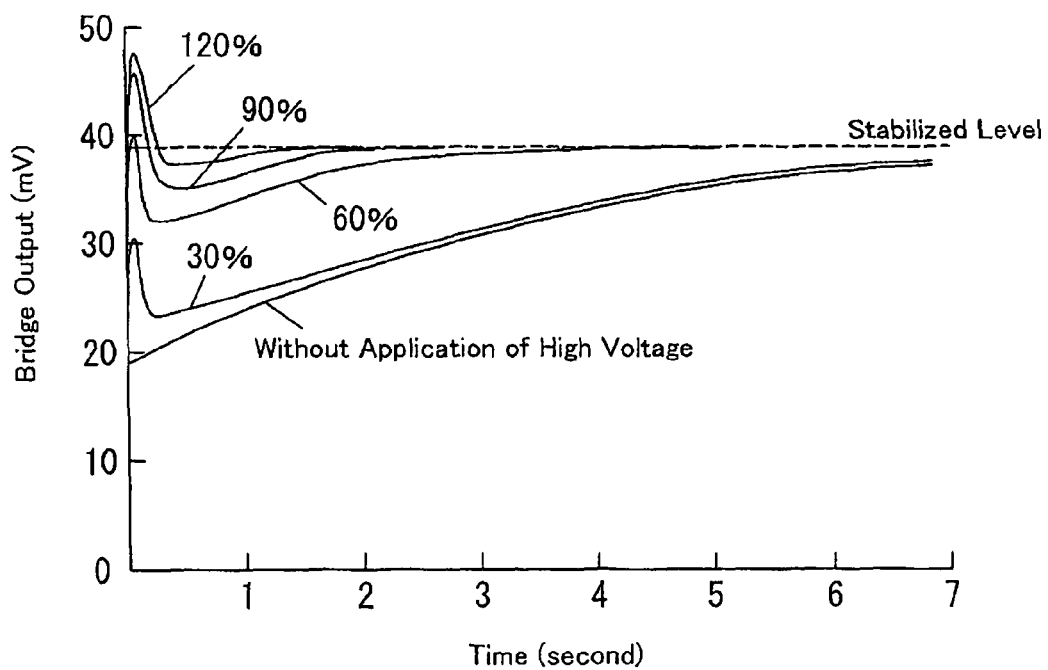
FIG. 10 is a graph showing the stabilization times measured with respect to specimen (1) with the detection element 1 of 0.6 mm outside diameter under a condition of applying a high voltage for 0.1 second while varying high voltage.
Figure 11:
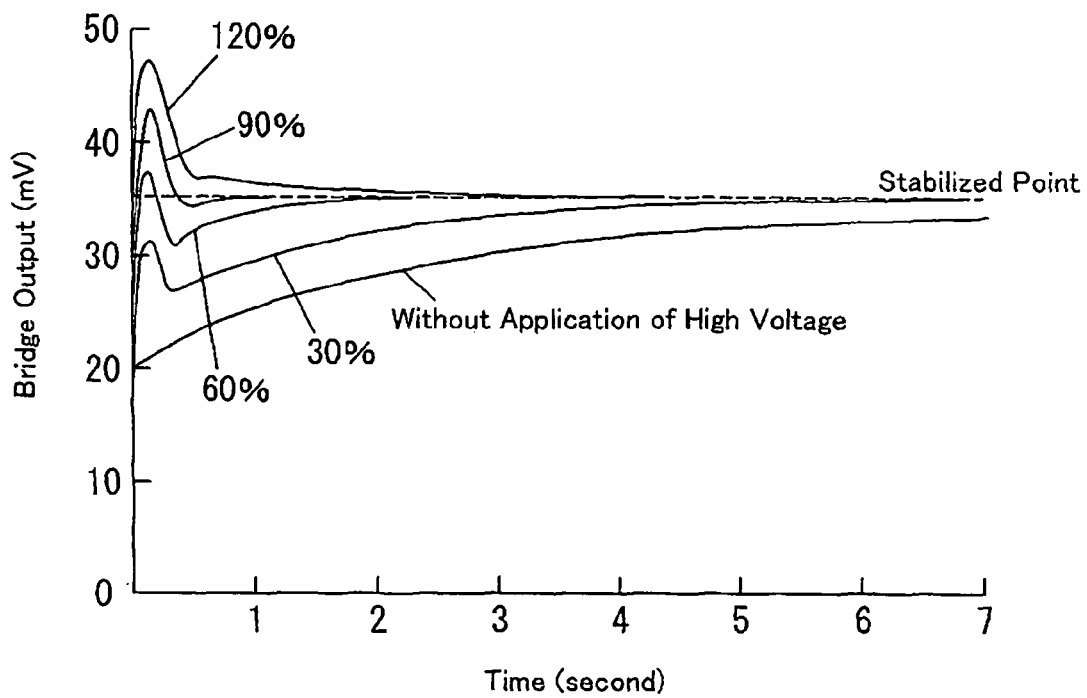
FIG. 11 is a graph showing the stabilization times measured with respect to specimen (1) with the detection element 1 of mm outside diameter under a condition of applying a high voltage for 0.3 second while varying high voltage.

And, a similar test was carried out in the atmosphere of the hydrogen concentration of 10000 ppm in place of the test in the ambient atmosphere. The results of the test are shown in Table 2. Further, the results when the outside diameter of the element was 0.6 mm and the application time was 0.1 second are graphed in FIG. 10 and the results when the outside diameter of the detection element 1 was 0.6 mm and the application time was 0.3 second are graphed in FIG. 11.

TABLE 2

| Outside diameter of the detection element | Conditions of high voltage mode | | | | |
|---|---|---|---|---|---|
| | | Applied voltage (percentage increase in voltage with respect to the normal voltage) | | | |
| | Application time | Increase by 30% | Increase by 60% | Increase by 90% | Increase by 120% |
| 0.4 mm | 0.1 sec | 4.3 sec | 0.8 sec | 0.8 sec | 3.6 sec |
| | 0.2 sec | 3.1 sec | 0.7 sec | 0.4 sec | 6.1 sec |
| | 0.3 sec | 2.2 sec | 0.6 sec | 0.6 sec | 7.2 sec |
| 0.5 mm | 0.1 sec | 8.6 sec | 1.0 sec | 0.4 sec | 2.1 sec |
| | 0.2 sec | 4.8 sec | 0.8 sec | 0.5 sec | 4.6 sec |
| | 0.3 sec | 3.5 sec | 0.8 sec | 0.6 sec | 5.3 sec |
| 0.6 mm | 0.1 sec | 16 sec | 4 sec | 1.8 sec | 1.2 sec |
| | 0.2 sec | 10 sec | 3.1 sec | 1.1 sec | 2.2 sec |
| | 0.3 sec | 6.5 sec | 2.0 sec | 0.8 sec | 3.9 sec |

From these results, the voltage switching between two levels is found effective to shorten the time for reaching stabilization in the ambient atmosphere and also in the atmosphere of a hydrogen concentration of 10000 ppm by the switch of the applied voltage between two stages.

Particularly in the cases where the outside diameters of the detection elements 1 are 0.4 mm to 0.5 mm, the high voltage in the high voltage mode was set at voltage values which are higher than in the normal mode by 60 to 90%, and an application time in the high voltage mode are set at 0.1 to 0.3 second, the stabilization time significantly reduced. Furthermore, even though the outside diameter of the elements is 0.6 mm or more, if the applied voltage is switched between three or more stages instead of two stages in the present example, there is a possibility that the stabilization time can be further reduced though this leads to the complication of the measuring circuit or cumbersome operational control.

(2) Specimen (2)

On the elements of specimen (2), a test similar to that on the elements of specimen (1) was carried out. The results of evaluations in the ambient atmosphere are shown in Table 3.

TABLE 3

| Outside diameter of the detection element | Conditions of the high voltage mode | | | | |
|---|---|---|---|---|---|
| | | Applied voltage (percentage increase in voltage with respect to the normal voltage) | | | |
| | Application time | Increase by 30% | Increase by 60% | Increase by 90% | Increase by 120% |
| 0.4 mm | 0.1 sec | 0.6 sec | 0.5 sec | 0.6 sec | 0.3 sec |
| | 0.2 sec | 0.4 sec | 0.6 sec | 0.5 sec | 0.6 sec |
| | 0.3 sec | 0.4 sec | 0.4 sec | 0.6 sec | 0.7 sec |
| 0.5 mm | 0.1 sec | 0.9 sec | 0.7 sec | 0.7 sec | 0.5 sec |
| | 0.2 sec | 0.8 sec | 0.6 sec | 0.4 sec | 0.5 sec |
| | 0.3 sec | 0.6 sec | 0.5 sec | 0.4 sec | 0.5 sec |
| 0.6 mm | 0.1 sec | 1.3 sec | 1.1 sec | 0.8 sec | 0.7 sec |
| | 0.2 sec | 0.9 sec | 0.8 sec | 0.8 sec | 0.7 sec |
| | 0.3 sec | 0.6 sec | 0.8 sec | 0.8 sec | 1.4 sec |

The results of evaluations in the atmosphere of the hydrogen concentration of 10000 ppm are shown in Table 4.

TABLE 4

| Outside diameter of the detection element | Conditions of the high voltage mode | | | | |
|---|---|---|---|---|---|
| | | Applied voltage (percentage increase in voltage with respect to the normal voltage) | | | |
| | Application time | Increase by 30% | Increase by 60% | Increase by 90% | Increase by 120% |
| 0.4 mm | 0.1 sec | 4.1 sec | 0.7 sec | 0.6 sec | 3.2 sec |
| | 0.2 sec | 3.0 sec | 0.6 sec | 0.5 sec | 4.9 sec |
| | 0.3 sec | 2.4 sec | 0.4 sec | 0.5 sec | 7.0 sec |
| 0.5 mm | 0.1 sec | 8.0 sec | 0.9 sec | 0.6 sec | 2.1 sec |
| | 0.2 sec | 4.5 sec | 0.7 sec | 0.6 sec | 4.6 sec |
| | 0.3 sec | 3.1 sec | 0.5 sec | 0.5 sec | 5.3 sec |
| 0.6 mm | 0.1 sec | 14 sec | 3.5 sec | 1.7 sec | 1.1 sec |
| | 0.2 sec | 9 sec | 2.9 sec | 1.1 sec | 2.0 sec |
| | 0.3 sec | 6 sec | 1.8 sec | 1.1 sec | 3.3 sec |

From these results, as with specimen (1), the voltage switching between two levels is found effective to shorten the time for reaching stabilization in the ambient atmosphere and also in the atmosphere of a hydrogen concentration of 10000 ppm by the switch of the applied voltage between two stages.

Particularly in the cases where the outside diameters of the detection elements 1 were 0.4 mm to 0.5 mm, the high voltage is higher than the normal voltage by 60 to 90%, and an application time in the high voltage mode is set at 0.1 to 0.3 second, the stabilization time is significantly reduced. Furthermore, even though the outside diameter of the elements is 0.6 mm or more, if the applied voltage is switched between three or more stages instead of two stages in the present example, there is a possibility that the stabilization time is further reduced though this leads to the complication of the measuring circuit or cumbersome operational control.

4. Dimensional Evaluation Test of Compensation Element

In the above characteristic evaluation test with switching of applied voltage on both specimen (1) and (2), following phenomenon occurred in the ambient atmosphere, as in the above characteristic evaluation test with constant applied voltage. In the case where heat capacity was balanced between compensation element 2 and the compensation element 2, the detection element 1 and the compensation element 2 were equal in a temperature raising rate, and consequently the bridge output became a constant value almost instantaneously. In a case where the detection element 1 is larger than the compensation element 2, since the temperature raising of the compensation element 2 is faster than that of the detection element 1, the bridge output value approaches 0 V from a negative side. Further, in the case where the detection element 1 is smaller than the compensation element 2, since the temperature raising of the detection element 1 was faster than that of the compensation element 2, the bridge output value approaches 0 V from a positive side. That is, when there is a difference in the dimension between the detection element 1 and the compensation element 2, there is a difference in the temperature raising rate between the detection element 1 and the compensation element 2 based on the difference of their heat capacities.

Therefore, when the detection element 1 is smaller than the compensation element 2, the bridge output value is shifted to the positive side upon energization of the hydrogen gas sensor even if hydrogen does not actually exist in an atmosphere, and a bridge output looking as if a hydrogen gas exists is produced. In order to avoid this, it is preferable that the dimension of the compensation element 2 is smaller than that of the detection element 1. In order to verify this, the following test was carried out.

On the elements of specimen (1) and (2), the detection element 1 having the outside diameter of 0.6 mm and the compensation element 2 having the outside diameter changed in the range of 100 to 90% of the outside diameter of the detection element 1 were used.

A plurality of samples were prepared for each combination of the detection element 1 and the compensation element 2, and a test similar to the above characteristic evaluation test with switching of applied voltage was carried out in an ambient atmosphere.

Start-up evaluation is also made to see whether the bridge output approaches toward a stabilized level at which the bridge output settles to constant, either from there below or there above, based on the bridge output value measured at 0.2 second from energization.

Figure 12:
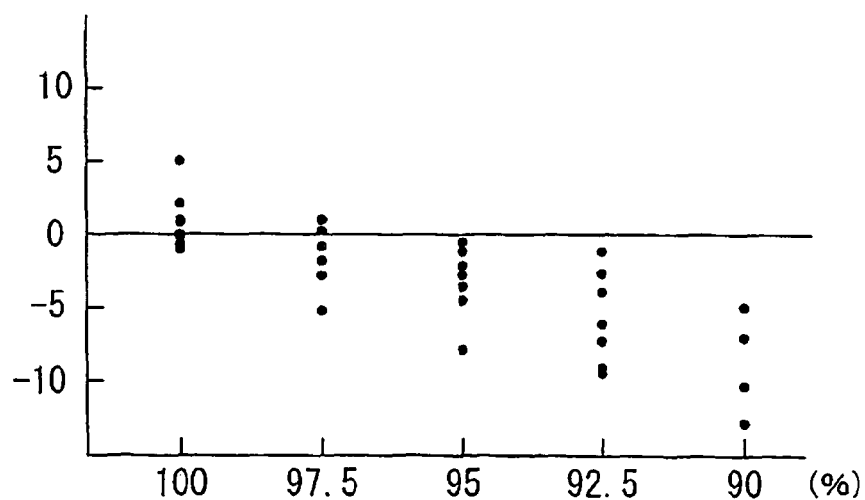
FIG. 12 is a graph showing the results of stabilization times in dimensional evaluation test of compensation element, measured with respect to specimen (1)
Figure 13:
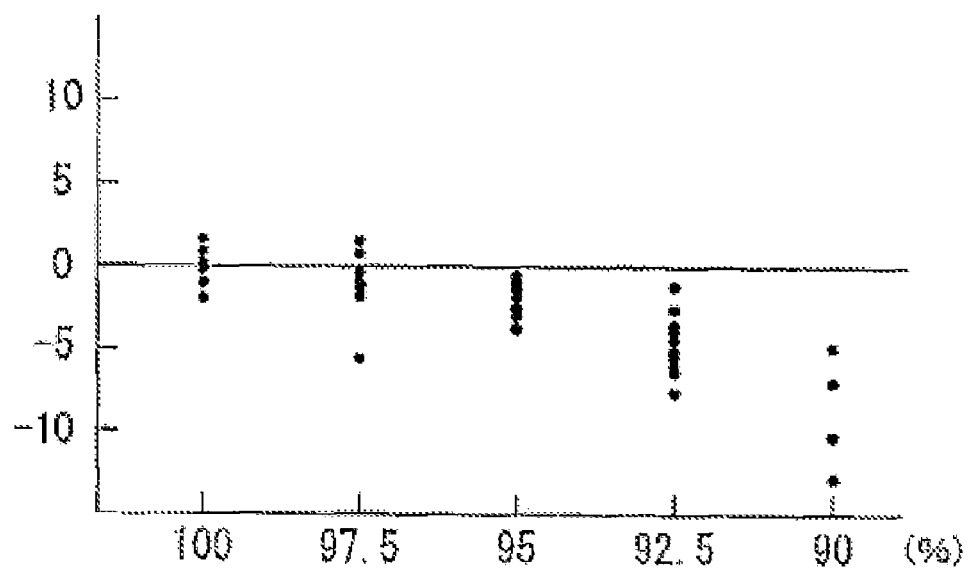
FIG. 13 is a graph showing the results of the stabilization time in the dimensional evaluation test of compensation element, measured with respect to specimen (2)
Figure 13:
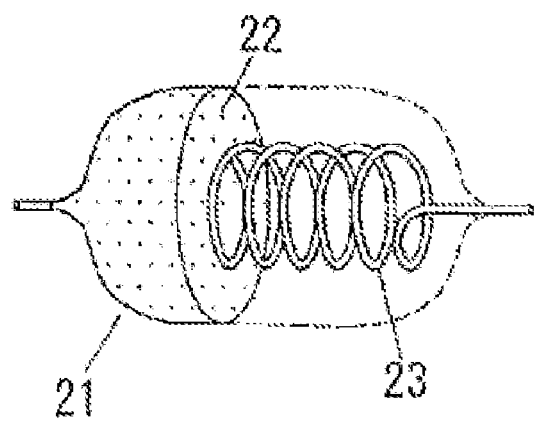

The results on specimen (1) are shown in FIG. 12 and the results on specimen (2) are shown in FIG. 13. From these results, it is found that as the detection element 1 is made smaller than the compensation element 2, the bridge output is more frequent to approach towards to the stabilized level from below. Particularly, with regard to the compensation element 2 which are 95% or less of the detection element 1, the bridge output is not found to approach to the stabilized level from the above. However, preferably, the dimensions of the detection element 1 and the compensation element 2 are similar to each other in order to make their thermal behavior compatible with each other. Therefore, it is considered that the dimension of the outside diameter of the compensation element 2 is preferably 90 to 95% of the dimension of the outside diameter of the detection element 1.

What is claimed is:

1. A hydrogen gas sensor of a catalytic combustion type with a detection element, said gas sensor comprising:
   a measuring circuit configured to selectively provide a normal voltage mode for applying a normal voltage to said detection element and a high voltage mode for applying a high voltage higher than said normal voltage to said detection element, and
   said detection element comprising: a platinum-made coil and a porous body for entrapping silicon compound covering said coil, said coil being configured to serve as a hydrogen combustion member, a heating member, and a temperature-sensing resistor.

2. A gas sensor as set forth in claim 1, wherein said measuring circuit is configured to first apply said high voltage which is 160% to 190% of the normal voltage to said detection element for a time period of 0.1 sec to 0.3 sec, and subsequently apply said normal voltage to said detection element.

3. A gas sensor as set forth in claim 1, wherein said detection element is shaped into a bead having an outside diameter of 0.3 mm to 0.6 mm.

4. A gas sensor as set forth in claim 1, wherein said gas sensor comprising a compensation element, and said compensation element is dimensioned to be smaller than said detection element.

5. A gas sensor as set forth in claim 1, wherein
   said measuring circuit is configured to first apply said high voltage, and subsequently apply said normal voltage to said detection element.

6. A gas sensor as set forth in claim 5, wherein said measuring circuit is configured to first apply said high voltage which is 160% to 190% of the normal voltage to said detection element for a time period of 0.1 sec to 0.3 sec, and subsequently apply said normal voltage to said detection element.

* * * * *